United States Patent [19]

Merger et al.

[11] Patent Number: 5,371,292

[45] Date of Patent: Dec. 6, 1994

[54] PREPARATION OF 3-AMINOMETHYL-3,5,5-TRIMETHYL-CYCLOHEXYLAMINE

[75] Inventors: Franz Merger, Frankenthal; Claus-Ulrich Priester; Tom Witzel, both of Ludwigshafen; Gerhard Koppenhoefer, Roemerberg; Wolfgang Harder, Weinheim, all of Germany

[73] Assignee: BASF Aktiengesellschaft, Ludwigshafen, Germany

[21] Appl. No.: 92,029

[22] Filed: Jul. 15, 1993

Related U.S. Application Data

[63] Continuation of Ser. No. 888,266, May 22, 1992, abandoned, which is a continuation of Ser. No. 676,183, Mar. 27, 1991, abandoned.

[30] Foreign Application Priority Data

Mar. 30, 1990 [DE] Germany .................. 4010227

[51] Int. Cl.$^5$ ............. C07C 209/24; C07C 209/48; C07C 209/52
[52] U.S. Cl. ................... 564/446; 564/248; 564/278; 564/448; 564/455; 564/490; 558/430
[58] Field of Search ........... 564/248, 278, 446, 448, 564/455, 490; 558/430

[56] References Cited

U.S. PATENT DOCUMENTS

| | | | |
|---|---|---|---|
| 2,583,729 | 1/1952 | Deanesly | 564/278 |
| 4,083,869 | 4/1978 | Isshiki et al. | 564/269 |
| 4,429,158 | 1/1984 | Disteldorf et al. | 564/446 |
| 4,806,690 | 2/1989 | Bowman | 564/446 |

FOREIGN PATENT DOCUMENTS

| | | | |
|---|---|---|---|
| 0042119 | 6/1981 | European Pat. Off. | 564/446 |
| 0394968 | 10/1990 | European Pat. Off. | |
| 3011656 | 10/1981 | Germany | 564/455 |
| 0972010 | 10/1964 | United Kingdom . | |

OTHER PUBLICATIONS

Norton et al., *J. Org. Chem.*, vol. 19, pp. 1054–1065 (1954).
Chemical Abstracts, vol. 109, Nr. 11, Sep. 12, 1988, Nr. 92 344k.

*Primary Examiner*—Allen J. Robinson
*Assistant Examiner*—Scott C. Rand
*Attorney, Agent, or Firm*—John H. Shurtleff

[57] ABSTRACT

A process for the preparation of 3-aminomethyl-3,5,5-trimethyl-cyclohexylamine from 3-cyano-3,5,5-trimethyl-cyclohexanone, wherein the following stages are carried out in discrete reaction chambers:

a) the 3-cyano-3,5,5-trimethyl-cyclohexanone is reacted in a first reaction chamber with excess ammonia over an acidic metal oxide catalyst at a temperature of from 20° to 150° C. and a pressure of from 15 to 500 bar, and b) in a second reaction chamber, the reaction product from stage a) is hydrogenated with hydrogen at a temperature of from 60° to 150° C. and a pressure of from 50 to 300 bar in the presence of excess ammonia over a catalyst containing cobalt, nickel, ruthenium, and/or some other noble metal, which catalyst optionally contains a basic component or is supported by neutral or basic supporting material.

19 Claims, No Drawings

PREPARATION OF 3-AMINOMETHYL-3,5,5-TRIMETHYL-CYCLOHEXYLAMINE

This application is a continuation of application Ser. No. 07/888,266, filed Mar. 22, 1992, now abandoned, which is a continuation of Ser. No. 07/676,183, filed Mar. 27, 1991, now abandoned.

The present invention relates to a novel process for the preparation of 3-aminomethyl-3,5,5-trimethyl-cyclohexylamine from 3-cyano-3,5,5-trimethyl-cyclohexanone.

EP-A 42, 199 describes a process for the preparation of primary mono- and di-amines by reacting oxo compounds, which may or may not contain other reducible groups, with ammonia and hydrogen in the presence of conventional hydrogenation catalysts, before which reaction the said oxo compounds are caused to enter into a preliminary reaction with ammonia at a temperature of from 10° to 200° C. and a pressure of from 1 to 300 bar in the presence of organic or inorganic ion exchangers in the ammonium form and serving as imine-forming catalysts. Using this process, 3-cyano-3,5,5-trimethyl-cyclohexanone (isophoronenitrile) has been converted to 3-aminomethyl-3,5,5-trimethyl-cyclohexylamine (isophoronediamine) by reaction in contact with ion exchangers and by conventional hydrogenation over cobalt catalysts in yields of up to 95%.

The said process suffers from the drawback that ion exchangers are necessary to achieve short residence times in the imination stage. The ion exchangers thus required to achieve short residence times in the isomerization stage (organic or inorganic ion exchangers, e.g. zeolites which are characterized by a molecular sieve structure) are not only costly but suffer from poor mechanical and thermal stability.

It is thus an object of the present invention to provide a process for the preparation of 3-aminomethyl-3,5,5-trimethyl-cyclohexylamine from 3-cyano-3,5,5-trimethyl-cyclohexanone which avoids the above drawbacks.

Accordingly, we have found a novel, improved process for the preparation of 3-aminomethyl-3,5,5-trimethyl-cyclohexylamine from 3-cyano-3,5,5-trimethyl-cyclohexanone, wherein the following stages are carried out in discrete reaction chambers:

a) the 3-cyano-3,5,5-trimethyl-cyclohexanone is reacted in a first reaction chamber with excess ammonia over an acidic metal oxide catalyst at a temperature of from 20° to 150° and a pressure of from 15 to 500 bar, and b) in a second reaction chamber, the reaction product from stage a) is hydrogenated with hydrogen at a temperature of from 60° to 150° C. and a pressure of from 50 to 300 bar in the presence of excess ammonia over a catalyst containing cobalt, nickel, ruthenium, and/or some other noble metal, which catalyst optionally contains a basic component or is supported by neutral or basic supporting material.

The process of the invention can be carried out as follows using two discrete reaction chambers:

a) In a first stage, a 3-cyano-3,5,5-trimethyl-cyclohexanone is reacted with excess ammonia at a temperature of from 20° to 150° C., preferably from 30° to 130° C. and more preferably from 50° to 100° C. and under a pressure of from 15 to 500 bar, preferably from 100 to 350 bar, to yield the 3-cyano-3,5,5-trimethyl-cyclohexylimine.

Suitable acidic metal oxide catalysts are aluminum oxide, silicon dioxide, titanium dioxide, and zirconium dioxide. These oxides do not have a molecular sieve structure. We prefer to use aluminum oxide, titanium dioxide, and zirconium oxide, particularly aluminum oxide and titanium dioxide. If desired, the acidity of the catalyst can be raised by doping it with a halide. Thus halide-doped catalysts may be used such as chloride on aluminum oxide or chloride on titanium dioxide.

For the imination a throughput of from 0.01 to 10 kg, preferably from 0.02 to 5 kg and more preferably from 0.05 to 3 kg, of 3-cyano-3,5,5-trimethyl-cyclohexanone per kg of catalyst per hour is maintained. The amount of $NH_3$ used per mole of 3-cyano-3,5,5-trimethyl-cyclohexanone during the imination is conveniently but not obligatorily from 5 to 500 moles, preferably from 30 to 400 moles and more preferably from 50 to 300 moles. The imination of the 3-cyano-3,5,5-trimethyl-cyclohexanone may also be carried out in the presence of a solvent such as an alkanol or tetrahydrofuran.

The imination is preferably carried out continuously in a pressure vessel or cascade of pressure vessels. In a preferred embodiment, the 3-cyano-3,5,5-trimethyl-cyclohexanone and $NH_3$ are passed through a tubular reactor containing the imination catalyst in the form of a fixed bed.

The overall residence time in stage a) is determined by the throughput rate and the amount of ammonia used. It is advantageously in the range of 0.5 to 120 minutes, preferably 1 to 40 minutes and more preferably 1.5 to 20 minutes.

b) The resulting product is passed to a second stage where it is subjected to catalytic hydrogenation involving from 3 to 10,000, preferably 4.5 to 30, mole equivalents of hydrogen, if necessary after the addition of a further amount of ammonia.

For the aminating hydrogenation, the temperature is kept at a value of from 60° to 150° C., preferably from 70° to 140° C. and more preferably from 80° to 130° C. and the pressure at a value between 50 and 500 bar, preferably between 100 and 350 bar and more preferably between 150 and 300 bar.

The throughput rate is advantageously in the range of 0.01 to 5 kg/kg/h, preferably 0.02 to 2.5 kg/kg/h and more preferably 0.05 to 2 kg/kg/h.

The hydrogenation is advantageously carried out in liquid ammonia. The amount of ammonia used per mole of 3-cyano-3,5,5-trimethyl-cyclohexylimine is preferably from 5 to 500 moles, more preferably from 30 to 400 moles and most preferably from 50 to 300 moles. It is convenient to select the same ammonia rate as is used in the preceding synthesis of 3-cyano-3,5,5-trimethyl-cyclohexylimine from the corresponding 3-cyano-3,5,5-trimethyl-cyclohexanone. Alternatively, the desired ammonia rate may be achieved by adding fresh ammonia to the ammonia stream prior to hydrogenation.

The aminating hydrogenation of the 3-cyano-3,5,5-trimethyl-cyclohexylimine is preferably carried out continuously, for example in a pressure-tight stirred vessel or a cascade of such vessels. In a particularly preferred embodiment, a tubular reactor is used in which the mixture of products leaving the imination of the 3-cyano-3,5,5-trimethyl-cyclohexanone is passed through a fixed catalyst bed acting either as a bubble bed or as a trickle bed.

The stages a) and b) may alternatively be carried out in a single reactor in which the imination and hydrogenation catalysts are in two separate layers, in which case the imination is conveniently carried out in the presence of hydrogen.

For continuous operation in a tubular reactor without recycling, the overall residence time is determined by the throughput rate and the amount of ammonia used. It ranges from 0.5 to 120 minutes, preferably from 1 to 40 minutes and more preferably from 1.5 to 20 minutes.

Following the hydrogenation, the excess ammonia is separated off, if necessary under pressure. The resulting 3-cyano-3,5,5-trimethyl-cyclohexylamine can be isolated by fractional distillation.

In principle, all commonly used hydrogenation catalysts can be employed n the hydrogenation stage, for example catalysts containing nickel, cobalt, iron, copper, ruthenium or any other noble metal in group VIII of the periodic table. We prefer to use ruthenium, cobalt or nickel catalysts, ruthenium and cobalt catalysts being particularly preferred. The catalytically active metals may be in the form of solid catalysts or supported catalysts. Examples of suitable supports are aluminum oxide, titanium dioxide, zirconium dioxide, zinc oxide, and magnesium oxide/aluminum oxide, and hydrogenation catalysts are preferred which contain basic components such as oxides and hydroxides of alkali metals and alkaline earth metals. Basic supports are therefore particularly preferred, e.g. $\beta$-aluminum oxide or magnesium oxide/aluminum oxide, especially magnesium oxide in which the content of magnesium oxide is from 5 to 40%. The support containing magnesium oxide and aluminum oxide may be amorphous or a spinel.

We particularly prefer to use cobalt or ruthenium with a content of basic components as hydrogenation catalyst. Such catalysts are produced industrially by conventional methods. For example, ruthenium on a basic support is obtained by depositing an aqueous ruthenium salt solution, e.g. ruthenium chloride or ruthenium nitrate, on to the appropriate support. The concentration of the ruthenium on the support ranges from 0.1 to 10%, preferably from 0.5 to 5% and more preferably from 1 to 4%. After drying and, possibly, after calcination at a temperature of from 120° to 500° C. and preferably from 200° to 400° C., the ruthenium catalyst is activated in a stream of hydrogen at a temperature of from 180° to 250° C. and preferably from 190° to 230° C. and under a pressure of from 1 to 500 bar, preferably from 20 to 300 bar, for a period of from 1 to 20 hours, preferably 2 to 10 hours.

The said ruthenium catalysts may optionally contain other metals, such as palladium or iron. The iron content is generally between 0.5 and 5% and the palladium content between 0.1 and 5%.

The ruthenium catalysts are characterized by the fact that they permit particularly high throughput rates and thus provide particularly high space-time yields.

The basic cobalt catalysts contain at least one basic component such as $Li_2O$, $Na_2O$, $K_2O$, MgO, CaO, SrO, or BaO. Besides this component, such catalysts contain at least one of the elements iron, nickel, manganese, chromium, molybdenum, tungsten, and phosphorus. Of particular interest are catalysts which contain, besides cobalt and a basic component, at least one of the metals iron, nickel, and manganese. The metals may be used in metallic form or in the form of their oxides. For all practical purposes, phosphorus is present in the form of phosphoric acid.

3-Aminomethyl-3,5,5-trimethyl-cyclohexylamine (isophoronediamine) is an important intermediate in the synthesis of diisocyanates and polyamides.

EXAMPLES

EXAMPLE 1

A vertical tubular reactor (diameter 16 mm, packing height 50 cm, oil-heated double jacket) was packed with 90.1 g (87 ml) of a catalyst containing 3% of ruthenium on $\beta$-aluminum oxide in the form of 1.2 mm extrudates (prepared by filling the pores of $\beta$-aluminum oxide with an aqueous ruthenium nitrate solution and drying at 120° C.). Reduction of the catalyst was effected by keeping it at a temperature of 220° C. for 9 hours under a stream of 150 standard liters of hydrogen per hour, under standard pressure, after the temperature had been progressively raised form 100° to 220° C. over a period of 7 hours.

Through a tubular reactor (diameter 16 mm, packing height 50 cm, oil-heated double jacket), installed upstream of the hydrogenation reactor and packed with 63.5 g (100 ml) of titanium dioxide (anatase) in the form of 1.5 mm extrudates there were passed upwardly, per hour, 80.4 g of a 50% solution of isophoronenitrile (purity 99.0%) in tetrahydrofuran and 303.0 g of liquid ammonia at a pressure of 250 bar and a temperature of 80° C. Hydrogen was then added to the stream at a rate of 60 standard liters (2.7 moles) per hour, and the effluent from the in-line imination reactor was passed upwardly through the hydrogenation reactor at a pressure or 250 bar and a temperature of 120° C. Gas-chromatographic analysis of the hydrogenation product gave 95.2% of isophoronediamine in addition to 0.8% of 1,3,3-trimethyl-6-azabicyclo[3.2.1]octane, corresponding to a diamine yield of 96.2% of theory.

EXAMPLE 2

A vertical tubular reactor (diameter 16 mm, packing height 50 cm, oil-heated double jacket) was packed with 183.1 g (100 ml) of a solid cobalt catalyst (CoO containing 5% of $Mn_2O_3$ and 3% of $P_2O_5$) in the form of 1 mm to 1.5 mm grit. Reduction of the catalyst was effected by keeping it at a temperature of 330° for 30 hours under a stream of 150 standard liters of hydrogen per hour after the temperature had been progressively raised from 100° to 330° C. over a period of 23 hours, all under a pressure of 100 bar.

Through a tubular reactor (diameter 16 mm, packing height 50 cm, oil-heated double jacket), installed upstream of the hydrogenation reactor and packed with 70.0 g (100 ml) of $\gamma$-aluminum oxide in the form of 1.5 mm extrudates there were passed upwardly, per hour, 25.4 g of a 50% solution of isophoronenitrile (purity 99.0%) in tetrahydrofuran and 303.0 g of liquid ammonia at a pressure of 250 bar and a temperature of 80° C. Hydrogen was then added to the stream at a rate of 60 standard liters (2.7 moles) per hour, and the effluent from the in-line imination reactor was passed upwardly through the hydrogenation reactor at a pressure of 250 bar and a temperature of 130° c. The effluent was depressurized to standard pressure, and the ammonia was distilled off. The hydrogenation product contained, apart from tetrahydrofuran, 94.1% of isophoronediamine and 1.4% of 1,3,3-trimethyl-6-azabicyclo[3.2.1]octane, as determined by gas-chromatographic analysis.

EXAMPLE 3

A vertical tubular reactor (diameter 16 mm, packing height 50 cm, oil-heated double jacket) was packed with 176.7 g (100 ml) of a solid basic cobalt catalyst (CoO containing 5% of $Mn_2O_3$ and 1.4% of $Na_2O$) in the form of 1 mm to 1.5 mm grit. Reduction of the catalyst was effected by keeping it at a temperature of 330° C. for 30 hours under a stream of 150 standard liters of hydrogen per hour after the temperature had been progressively raised form 100° to 330° C. over a period of 23 hours, under a pressure of 100 bar.

Through a tubular reactor (diameter 16 mm, packing height 50 cm, oil-heated double jacket), installed upstream of the hydrogenation reactor and packed with 70.0 g (100 ml) of γ-aluminum oxide in the form of 1.5 mm extrudates there were passed upwardly, per hour, 40.4 g of a 50% solution of isophoronenitrile (purity 99.0%) in tetrahydrofuran and 303.0 g of liquid ammonia at a pressure of 250 bar and a temperature of 80° C. Hydrogen was then added to the stream at a rate of 60 standard liters (2.7 moles) per hour, and the effluent from the in-line imination reactor was passed upwardly through the hydrogenation reactor at a pressure of 250 bar and a temperature of 130° C. The effluent was depressurized to standard pressure, and the ammonia was distilled off. The hydrogenation product contained, apart from tetrahydrofuran, 96.4% of isophoronediamine and 0.6% of 1,3,3-trimethyl-6-azabicyclo[3.2.1]octane, as determined by gas-chromatographic analysis. The product obtained over an on-stream period of 121 hours was collected and separated by fractional distillation. There were obtained 2,371 g of isophoronediamine, corresponding to a yield of 95.1%.

EXAMPLE 4

A vertical tubular reactor (diameter 16 mm, packing height 50 cm, oil-heated double jacket) was packed with 176.7 g (100 ml) of a basic solid cobalt catalyst (CoO containing 5% of $Mn_2O_3$ and 1.4% of $Na_2O$) in the form of 1 mm to 1.5 mm grit. Reduction of the catalyst was effected by keeping it at a temperature of 330° C. for 30 hours under a stream of 150 standard liters of hydrogen per hour after the temperature had been progressively raised from 100° to 330° C. over a period of 23 hours, under a pressure of 100 bar.

Through a tubular reactor (diameter 16 mm, packing height 50 cm, oil-heated double jacket), installed upstream of the hydrogenation reactor and packed with 70.0 g (100 ml) of γ-aluminum oxide in the form of 1.5 mm extrudates there were passed upwardly, per hour, 13.8 g of molten isophoronentrile (purity 99.0%) and 303.0 g of liquid ammonia at a pressure of 250 bar and a temperature of 80° C. Hydrogen was then added to the stream at a rate of 60 standard liters (2.7 moles) per our, and the effluent from the in-line imination reactor was passed upwardly through the hydrogenation reactor at a pressure of 250 bar and a temperature of 130° C. The hydrogenation product was depressurized to standard pressure, and the ammonia was distilled off. The resulting product contained, apart from tetrahydrofuran, 97.7% of isophoronediamine and 0.3% of 1,3,3-trimethyl-6-azabicyclo[3.2.1]octane, as determined by gas-chromatographic analysis, corresponding to a diamine yield of 98.7%.

We claim:

1. A process for the preparation of 3-aminomethyl-3,5,5-trimethyl-cyclohexanone from 3-cyano-3,5,5-trimethyl-cyclohexanone which comprises carrying out the following stages in discrete reaction chambers:
   a) reacting the 3-aminomethyl-3,5,5-trimethyl-cyclohexanone in a first reaction chamber with excess ammonia over an acidic metal oxide catalyst selected from the group consisting of aluminum oxide, silicon dioxide, titanium dioxide and zirconium dioxide, at a temperature of from 20° to 150° C. and a pressure of from 15 to 500 bar; and
   b) in a second reaction chamber, hydrogenating the reaction product from stage a) with hydrogen at a temperature of from 60° to 150° C. and a pressure of from 50 to 300 bar in the presence of excess ammonia over a hydrogenation catalyst containing at least one metal selected from the group consisting of cobalt, nickel, iron, copper and a noble metal in group VIII of the periodic table.

2. A process as claimed in claim 1, wherein the hydrogenation catalyst also includes as a basic component, an oxide or hydroxide of an alkali metal or alkaline earth metal.

3. A process as claimed in claim 1, wherein the hydrogenation catalyst is supported on a neutral or basic supporting material.

4. A process as claimed in claim 1, wherein the hydrogenation catalyst is supported on an oxide support selected from the group consisting of aluminum oxide, titanium dizirconium dioxide, oxide, zinc oxide and magnesium oxide/aluminum oxide.

5. A process as claimed in claim 1, wherein the hydrogenation catalyst is selected from the group consisting of cobalt and ruthenium on a basic supporting material.

6. A process as claimed in claim 1, wherein the acidic metal oxide catalyst is aluminum oxide.

7. A process as claimed in claim 1, wherein the acidic metal oxide catalyst is titanium dioxide.

8. A process as claimed in claim 1, wherein the acidic metal oxide catalyst is doped with a halide to raise its acidity.

9. A process as claimed in claim 8, wherein the catalyst is doped with a chloride.

10. A process as claimed in claim 1, wherein the process is carried out continuously through both stages with an overall residence time in stage a) of about 0.5 to 120 minutes.

11. A process as claimed in claim 10, wherein the residence time is about 1 to 40 minutes.

12. A process as claimed in claim 10, wherein the residence time is about 1.5 to 20 minutes.

13. A process as claimed in claim 1, wherein the hydrogention catalyst is ruthenium containing up to 5% of iron or palladium.

14. A process as claimed in claim 1, wherein the hydrogenation catalyst is ruthenium containing from about 0.5 to 5% of iron.

15. A process as claimed in claim 1, wherein the hydrogenation catalyst is ruthenium containing from about 0.1 to 5% of palladium.

16. A process as claimed in claim 1, wherein the hydrogenation catalyst is cobalt containing a basic component selected from the group consisting of alkali metals and alkaline earth metals.

17. A process as claimed in claim 16, wherein the basic cobalt catalyst contains at least one additional element selected from the group consisting of iron, nickel, manganese, chromium, molybdenum, tungsten and phosphorous.

18. A process as claimed in claim 16, wherein the basic cobalt catalyst contains at least one additional metal selected from the group consisting of iron, nickel and manganese.

19. A process as claimed in claim 1, wherein the process is carried out continuously with a throughput of about 0.01 to 5 kg/kg/hr, using liquid ammonia in an amount of about 5 to 500 moles per mole of the 3-cyano-3,5,5-trimethylcyclohexylimine as formed in the first stage.

* * * * *

UNITED STATES PATENT AND TRADEMARK OFFICE
CERTIFICATE OF CORRECTION

PATENT NO. : 5,371,292
DATED : December 6, 1994
INVENTOR(S) : Merger et al.

It is certified that error appears in the above-identified patent and that said Letters Patent is hereby corrected as shown below:

IN THE CLAIMS:

Col. 5, line 68,
 Claim 1, line 2: change "-cyclohexanone" to read
-- -cyclohexylamine --.

Col. 6, line 3,
 Claim 1, line 5: after "a) reacting the", change
"3-aminomethyl-" to read -- 3-cyano- --.

Col. 6, line 28,
 Claim 4, line 4: after "titanium", delete
"dizirconium dioxide, oxide," and substitute
-- dioxide, zirconium dioxide, --.

Signed and Sealed this

Twenty-first Day of February, 1995

Attest:

BRUCE LEHMAN

Attesting Officer

Commissioner of Patents and Trademarks